United States Patent
Li

(10) Patent No.: US 12,343,260 B2
(45) Date of Patent: Jul. 1, 2025

(54) METHOD FOR LIMITING DIFFUSION OF WEAR DEBRIS OF IN VIVO IMPLANT

(71) Applicant: Kai Li, Taiyuan (CN)

(72) Inventor: Kai Li, Taiyuan (CN)

(*) Notice: Subject to any disclaimer, the term of this patent is extended or adjusted under 35 U.S.C. 154(b) by 774 days.

(21) Appl. No.: 17/298,663

(22) PCT Filed: Dec. 13, 2019

(86) PCT No.: PCT/CN2019/124994
§ 371 (c)(1),
(2) Date: May 31, 2021

(87) PCT Pub. No.: WO2020/135088
PCT Pub. Date: Jul. 2, 2020

(65) Prior Publication Data
US 2022/0015910 A1    Jan. 20, 2022

(30) Foreign Application Priority Data

Dec. 26, 2018 (CN) .......................... 201811603775.2

(51) Int. Cl.
*A61F 2/30* (2006.01)
(52) U.S. Cl.
CPC ...... *A61F 2/30767* (2013.01); *A61F 2002/30685* (2013.01); *A61F 2002/30939* (2013.01)
(58) Field of Classification Search
CPC .. A61F 2002/30682; A61F 2002/30683; A61F 2002/30685
See application file for complete search history.

(56) References Cited

U.S. PATENT DOCUMENTS

| | | |
|---|---|---|
| 5,514,182 A | 5/1996 | Shea |
| 5,702,483 A | 12/1997 | Kwong |
| 5,755,807 A * | 5/1998 | Anstaett ............... A61F 2/32 623/22.2 |
| 6,706,071 B1 | 3/2004 | Wolter |
| 2003/0032958 A1 | 2/2003 | Soubeiran |

(Continued)

FOREIGN PATENT DOCUMENTS

| | | |
|---|---|---|
| CN | 105055007 A | 11/2015 |
| CN | 206534675 U | 10/2017 |
| CN | 109846537 A | 6/2019 |

(Continued)

*Primary Examiner* — Javier G Blanco
(74) *Attorney, Agent, or Firm* — SZDC Law PC

(57) ABSTRACT

Disclosed are a method for limiting diffusion of wear debris of an in vivo implant and an in vivo implant apparatus with a function of limiting wear debris. An elastomer seal is arranged at a wearing part between implant components that can move relatively and generate wear, such that an outlet for wear debris of the implant is always sealed within a sealing area formed by the seal and the implant components, thereby preventing the wear debris from diffusing outwards. The elastomer seal includes at least one flexible buffer part for reducing or completely offsetting relative motion between the implant components, thereby further reducing wear of a sealing part of the elastomer seal due to the relative motion between the parts. The seal is tightly attached to in vivo implant components, and the in vivo implant is smaller than a force for driving the components to generate relative motion.

2 Claims, 6 Drawing Sheets

(56) References Cited

U.S. PATENT DOCUMENTS

2008/0195104 A1     8/2008   Sidebotham et al.
2017/0281351 A1*   10/2017   Hubbard .................. A61F 2/32

FOREIGN PATENT DOCUMENTS

| EP | 2298244 B1 | 5/2017 |
|----|------------|--------|
| JP | H07289562 A | 11/1995 |
| JP | 2004024868 A | 1/2004 |
| JP | 2018021132 A | 2/2018 |
| WO | 0241808 A1 | 5/2002 |

* cited by examiner

METHOD FOR LIMITING DIFFUSION OF WEAR DEBRIS OF IN VIVO IMPLANT

This application is the National Stage Application of PCT/CN2019/124994, filed on Dec. 13, 2019, which claims priority to Chinese Patent Application No. 201811603775.2, filed on Dec. 26, 2018, which is incorporated by reference for all purposes as if fully set forth herein.

TECHNICAL FIELD

The present invention relates to the field of an in vivo implant of orthopedics, and in particular to a method for limiting diffusion of wear debris of an in vivo implant.

BACKGROUND

For an in vivo implant of orthopedics, for example, a spinal magnetic growth rod, a spinal growth guide rod, an extending femoral nail, and an assembled-type hip prosthesis, there is relative sliding among various components. Sliding may or may not be visible to naked eyes, but the sliding may generate wear debris, which diffuses to the outside of the in vivo implant through a clearance formed by a friction interface. These wear debris particles may result in inflammatory reactions in surrounding tissues, releasing metal ions and causing a metal disease. If the in vivo implant is made of other materials such as polyethylene, PEEK, and other materials, the wear debris is also generated, causing local inflammatory reactions.

It is mentioned in Spine Volume 43, Number 1, pp E16-E22 that the magnetic growth rod provides an O-ring seal between sleeve parts that move relatively, limiting the wear debris, but when taking out the in vivo implant, a patient found that 53% of sealing rings were damaged. A high damage rate of the O-ring seal may be related to limited space between moving components and limited space for accommodating the sealing ring. Due to a small sealing ring, an amount of wear, even though not large, is enough to make the sealing ring fail. Moreover, the sealing ring is small in size and limited in elasticity, and slight deformation may exceed an elastic range of the sealing ring, resulting in a dramatic rise in a pressure of the friction interface, a sharp increase in a friction force and increased wear. As shown in FIG. 11, adopt a magnetic growth rod with a conventional O-ring seal, although the sealing ring is elastic, a seal is formed between the sealing ring and an inner component and an outer component within the growth rod to achieve a sealing effect. When the inner component and the outer component of the growth rod have a micro-motion or even an obvious stretching motion, a relative motion amount between the inner component and the outer component will be directly transferred and converted into relative motion wear between the sealing ring and the components. After a period of time, elasticity of the sealing ring fails and even the sealing ring is broken, the seal fails, and the wear debris diffuses again and directly contacts with human tissues, resulting in adverse effects such as inflammation. FIG. 12 is a state after the wear debris diffuses and contacts with the human tissues.

Therefore, it is necessary to seek a method that has a lower failure probability and can limit escaping of wear debris and reduce an impact on patients in a special use environment of the in vivo implant of orthopedics.

SUMMARY

The present invention provides a method for limiting wear debris of an in vivo implant of orthopedics to solve the problem of an adverse effect of diffusion of wear debris of an existing in vivo implant of orthopedics on patients.

The present invention adopts the following technical solutions:

A method for limiting diffusion of wear debris of an in vivo implant, where an elastomer seal is arranged at a wearing part between implant components that can move relatively and generate wear, such that an outlet for wear debris of the implant is always sealed within a sealing area formed by the seal and the implant components, thereby preventing the wear debris from diffusing outwards; and The elastomer seal includes at least one flexible buffer part for reducing or completely offsetting relative motion between the implant components, thereby further reducing wear of a sealing part of the elastomer seal due to the relative motion between the parts.

The buffer part of the elastomer seal is disposed at the outlet for the wear debris of the implant.

The flexible buffer part is an elastic deformation volume or/and an additional axial retractable structure of an elastic sealing component itself.

An in vivo implant apparatus with a function of limiting wear debris, where the in vivo implant apparatus includes an implant formed by inserting and fitting an inner component and an outer component, the inner component and the outer component can relatively move to generate wear debris, an outlet for the wear debris of the implant is located at a port of the outer component that is cooperatively connected to the inner component, an elastomer seal is disposed on an insert fitting segment of the inner component and the outer component, where one part of the elastomer seal is tightly attached to a sleeve and is disposed on the inner component, and the other part of the elastomer seal is tightly attached to and connected with the outer component, the elastomer seal, the inner component and the outer component to form a sealing area wrapping the outlet for the wear debris, and a flexible buffer part is disposed between a sealing location on the inner component and a sealing location on the outer component.

The elastomer seal has an integrated structure, the elastomer seal is internally sleeved and connected to the outer component, an inner hole of the elastomer seal is cone-shaped and the elastomer seal is flange-shaped, an inner wall at a small end of the elastomer seal is tightly attached to the inner component to form a seal and the elastomer seal can move relative to the inner component, an inner wall of a boss at a large end of the elastomer seal and the inner component constitute the flexible buffer part through a clearance fit, and the boss at the large end of the elastomer seal is clamped in an inner hole of the outer component in a fixed manner.

The large end of the elastomer seal is in transitional connection with the inner hole of the outer component through a fixing apparatus in which a through-hole is provided for inserting and installing the inner component, one end of the fixing apparatus has a multi-lobe arrow shape and is inserted into and connected to the outer component through pressing, the other end of the fixing apparatus is internally provided with an annular notch with a diameter larger than that of the through hole, an end head of the boss at the large end of the elastomer seal is clamped in the annular notch, two axial end surfaces of the end head of the boss at the large end and the annular notch are in an interference fit, and a radial outer wall surface and the annular notch are in a clearance fit.

The fixing apparatus is made of a medical metal material or an implant material that can be used in vivo such as polyethylene, PU, and PEEK.

The elastomer seal has an integrated structure, the elastomer seal is externally sleeved and connected to the outer component, two ends of the inner hole of the elastomer seal are tightly attached to an outer wall of the inner component and an outer wall of the outer component respectively to form a seal and the elastomer seal can move relative to the inner component or the outer component, and the elastomer seal constitutes the flexible buffer part across variable diameter segments, of the inner component and the outer component, with different outer diameters.

The elastomer seal and the outer wall of the outer component are fixed through clamping with the boss.

A tight attaching force for realizing the seal between the elastomer seal and the inner component is provided by an accessory sleeved on the outer wall of the elastomer seal, and the accessory exerts tension on the elastomer seal from outside to inside in a radial direction.

A non-rigid structure that prevents the accessory from falling out is connected between the accessory and the outer component, and the non-rigid structure is in a normal loose state and does not transmit motion of the outer component to the elastomer seal through the non-rigid structure.

The elastomer seal has a split structure and includes three parts: the flexible buffer part, a sealing ring, and a ferrule, an inner ring of the sealing ring is tightly sleeved on the inner component, an outer ring of the sealing ring is tightly fixed by the ferrule and the outer ring of the sealing ring and the ferrule cannot move relatively, one end of the flexible buffer part is fixed and connected to the ferrule, and the other end is fixed and connected to an end head of the outer component.

An axial length of the ferrule is larger than an axial length of the sealing ring, an annular slot is provided in the ferrule, and the sealing ring is clamped in the annular slot in a fixed manner.

The buffer part is an elastic smooth surface or a retractable and foldable corrugated surface.

Several micropores are evenly distributed on the elastomer seal for balancing an inner side pressure and an outer side pressure of the seal.

According to the present invention, the seal is tightly attached to in vivo implant components, such that the wear debris cannot escape, and a friction force between the seal and the in vivo implant is smaller than a force for driving the components to generate relative motion, such that the relative motion between the components may not be blocked, thereby solving the problem of wear debris escaping. Moreover, a force that maintains tight attachment between the seal and the in vivo implant at the seal originates from tension of the seal itself or accessories that are not connected or rigidly connected with other components. In this case, when the components move relatively within an elastic range of the seal, because elasticity of a buffer segment of the seal acts as a buffer, the seal and the components to which the seal is tightly attached still maintain relative still. Furthermore, a sealing pressure in between is slightly affected. An interface pressure of the seal and the in vivo implant will not be changed dramatically due to relative motion between the components. Meanwhile, due to elasticity of the seal, accessories of the seal are not rigidly connected with the in vivo implant. The micro-motion between the components will not result in relative motion between the seal and the in vivo implant, thereby avoiding wear. In addition, the micro-motion between the in vivo implant components is very small relative to a deformation capacity of an elastic sleeve, and a possibility of fatigue failure of the elastic sleeve is very low.

The present invention has the following beneficial effects: According to the present invention, a seal is adopted to seal a clearance formed by a friction interface, wear debris particles are limited inside the in vivo implant, thereby reducing contact between wear debris and patient bodies, and decreasing an opportunity of producing adverse effects, and meanwhile, the seal does not prevent relative sliding of devices. The seal itself is not easy to wear or undergo fatigue failure.

Figure 1:
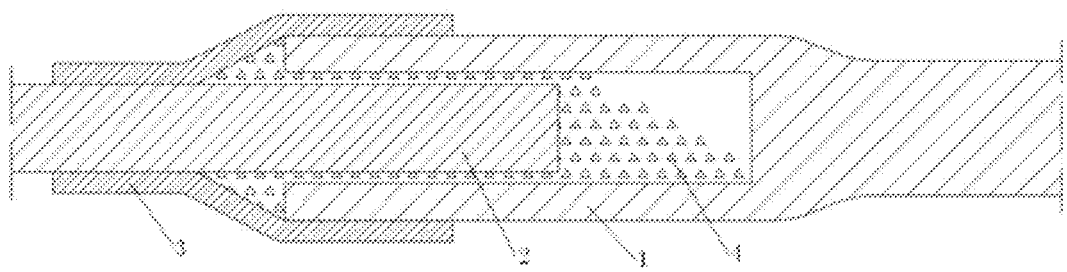
FIG. 1 is a schematic structural diagram of Embodiment 1 of the present invention.

Where: 1—outer component, 2—inner component, 3—elastomer seal, 4—wear debris, 5—flexible buffer part, 6—accessory, 7—fixing apparatus, 8—flexible buffer part, 9—sealing ring, 10—ferrule, and 11—micropore.

DETAILED DESCRIPTION

According to the present invention, an elastomer seal is arranged at a wearing part between implant components that can move relatively and generate wear, such that an outlet for wear debris of the implant is always sealed within a sealing area formed by the seal and the implant components, thereby preventing the wear debris from diffusing outwards; and the elastomer seal includes at least one flexible buffer part for reducing or completely offsetting an wear amount of relative motion for the elastomer seal during relative motion between the implant components. That is, micro-motions among the implant components in an axial, radial, torsional directions and the like may be directly absorbed through the flexible buffer part, in this case, there is no relative motion wear between the elastomer seal and the implant components. Only when a buffer stroke of the buffer part is insufficient to offset an axial motion stroke between implants (for example, as a body grows, a relative motion amount between the inner component and the outer component of implants such as a spinal growth rod of a teenage is obvious) can the elastomer seal slide relative to the implant, thus avoiding fracture due to excessive pulling.

The buffer part of the elastomer seal is disposed at the outlet for the wear debris of the implant. In this way, first, space for storing the wear debris is formed, and second, the outlet for the wear debris is where relative retractable segments of the inner component and the outer component are, the micro-motion between the inner component and the outer component may be directly absorbed by the buffer part, which in turn will not directly convert a motion between the inner component and the outer component into a motion between the elastomer seal and the components, thereby effectively avoiding or reducing wear of elastomer seal.

The flexible buffer part is an elastic deformation volume or/and an additional axial retractable structure of an elastic sealing component itself. That is, the elastic deformation volume of the sealing member itself may be used to absorb and offset the micro-motion stroke between the implant components. When a relative motion between implant components is relatively large, the buffer part may be designed to be a retractable and foldable corrugated segment to enhance an absorption effect of the buffer part of the elastomer seal.

The elastomer seal is mostly made of medical silica gel or PU and other materials. Under the premise of conforming to medical implantation, elastic materials are selected.

However, there are different ways of structural forms of the elastomer seal and connections between the seal and the inner component and the outer component, and the specific embodiments in which different seals are adopted in the present invention will be further explained below with reference to the drawings.

Embodiment 1

The in vivo implant apparatus having a function of limiting wear debris as shown in FIG. 1 includes formed by inserting and fitting an inner component and an outer component, the inner component and the outer component can relatively move to generate wear debris, an outlet for the wear debris of the implant is located at a port of the outer component that is cooperatively connected to the inner component, an elastomer seal is disposed on an insert fitting segment of the inner component and the outer component. The elastomer seal, the inner component and the outer component form a sealing area wrapping the outlet for the wear debris. Two ends of the inner hole of the elastomer seal are tightly attached to an outer wall of the inner component and an outer wall of the outer component respectively to form a seal and the elastomer seal constitutes the flexible buffer part across variable diameter segments, of the inner component and the outer component, with different outer diameters. In this case, the seal, the inner component and the outer component form a sealing area that may wrap the wear debris, to prevent diffusion of the wear debris and contacting with the human tissues. A seal structure of the embodiment forms an effective connection with the inner component and the outer component through elastic tension of the seal itself, and the elastic component can move relative to the inner component or the outer component.

A material of a buffer part segment may be the same as or different from that of a body of the seal. An outer surface of the elastomer seal of the buffer part may be a flat and smooth surface, or may be provided with a corrugated folding structure, that is, a buffer segment itself also has a certain amount of stretching.

Embodiment 2

Figure 2:
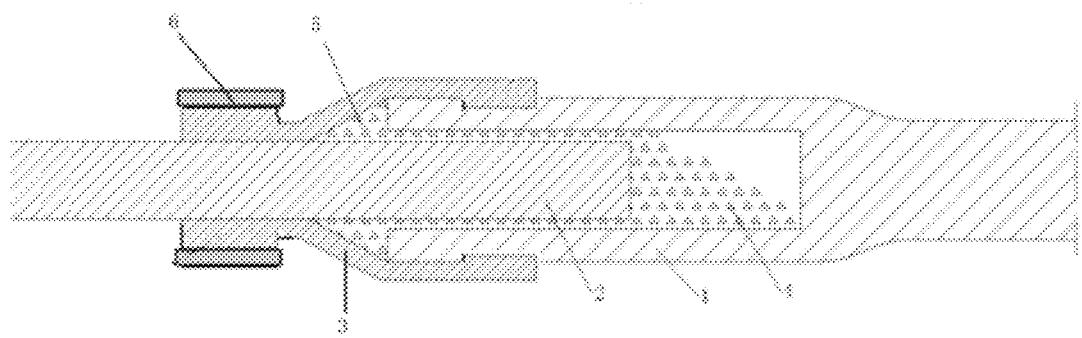
FIG. 2 is a schematic structural diagram of Embodiment 2 of the present invention.

As shown in FIG. 2, the structure is further optimized based on the structure of the seal described in Embodiment 1. To ensure an effective connection between the seal and the inner component and the outer component and to ensure a sealing effect, accessories are arranged on an outer wall of the elastomer seal connected with the inner component, while outer wall fixing through clamping with the elastomer seal and an outer wall of the outer component is completed through providing a clamping boss with an annular protrusion on the outer wall of the outer component, and then mutually clamping a head at a large end of the seal with the clamping boss. The accessories can adopt a filiform, band, shell, ring and the like of various materials, that is, to apply a radial force to a small end of the elastomer seal. To ensure that a distance from the outer component is kept within a certain range, the accessories and the outer component can be further connected through flexible structures that cannot extend axially, such as fixed wires, flexible connecting sleeves and the like.

Embodiment 3

Figure 3:
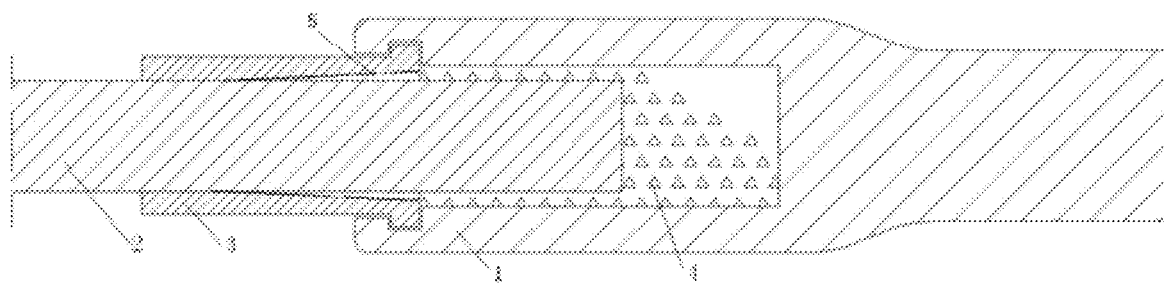
FIG. 3 is a schematic structural diagram of Embodiment 3 of the present invention.

In the structure as shown in FIG. 3, the elastomer seal is flange-shaped (T-shaped structure). A connection between an inner wall at a small end of the elastomer seal and the inner component is the same as that of Embodiment 1, and the elastomer seal is connected to the outer component by means of internal clamping connection. Moreover, an inner hole of the elastomer seal is cone-shaped and the small end of the inner hole is tightly attached to the inner component to realize the sealing effect, while a diameter of the large end of the inner hole is slightly larger than a diameter of the inner component, and this segment constitutes a flexible buffer segment. When the inner component and the outer component have relative micro-motion, a micro-motion amount can be offset and absorbed by a permeable buffer segment, thus effectively preventing micro-motion formation between the inner component and the outer component from transferring and forming motion wear between the seal and the inner component, thereby enhancing the sealing effect. The boss at the large end of the elastomer seal is clamped in an inner hole of the outer component in a fixed manner. The inner hole of the outer component is provided with an annular notch larger than a through-hole of the outer component. An end head of the boss of the elastomer seal is clamped in the annular notch, two axial end surfaces of the end head of the boss at the large end and the annular notch are in an interference fit, and a radial outer wall surface and the annular notch are in a clearance fit. That is, an axial end face of the boss of the elastomer seal is tightly attached to two side walls of the annular notch to form a seal, but the boss has a certain radial movement allowance in the annular notch.

Embodiment 4

Figure 4:
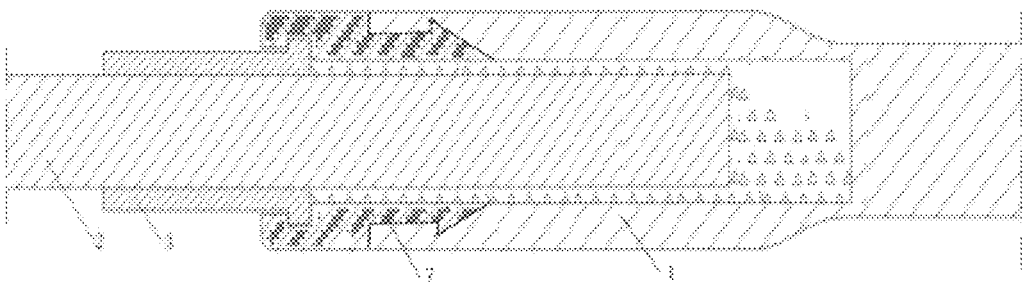
FIG. 4 is a schematic structural diagram of Embodiment 4 of the present invention.

Due to the need to ensure tight attachment of an elastic component with the inner component and the outer component, a structure of the elastic component in Embodiment 3 may have a difficulty in installing the elastomer seal during actual installing. Therefore, a fixing apparatus for transition is added between the seal and the outer component. The fixing apparatus is as shown in FIG. 4. An internally provided diameter is larger than that of the through-hole of the inner component. A left segment has a cylindrical shape, and a same annular slot as that in Embodiment 3 is provided on the left segment. A right segment has an arrow shape and is formed by combining three petals. By pressing radially, arrowheads with the three petals can be gathered inwards and pressed into the outer component while shape arrows of the right segment serve to clamp tightly and prevent falling off.

Embodiment 5

Figure 5:
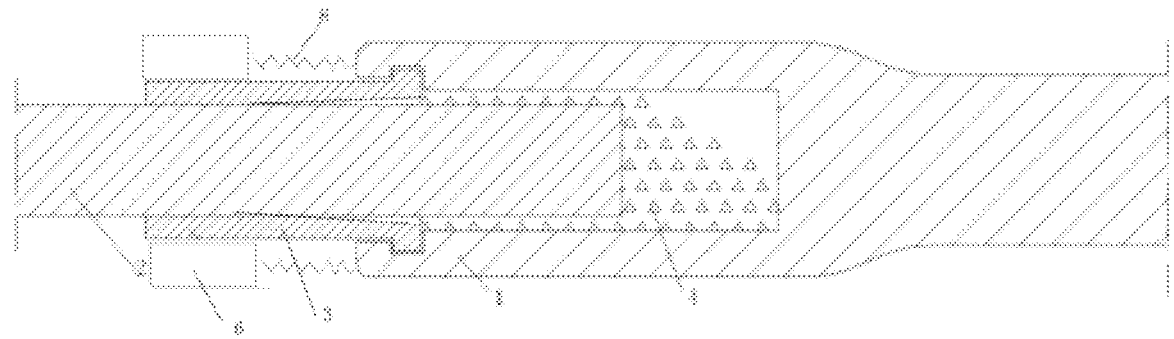
FIG. 5 is a schematic structural diagram of Embodiment 5 of the present invention.

The structure is as shown in FIG. 5. The structure of the seal is the same as those in Embodiments 3 and 4, except that an accessory is sleeved on an outer wall of an elastic sealing ring at a connection between the elastomer seal and the inner component. The accessory applies tension to the elastomer seal from outside to inside in a radial direction, and connects the accessory to the outer component of the in vivo implant through a non-rigid structure such as a spring or a flexible material. However, the non-rigid structure should enable applying a radial force to a small end of the elastomer seal. To keep a distance from the outer component within a certain range, the accessories and the outer component are connected through flexible structures that cannot extend axially, such as fixed wires, flexible connecting sleeves and the like so as to prevent from falling off without transmitting motion of the outer component of the in vivo implant to the seal.

Embodiment 6

Figure 6:
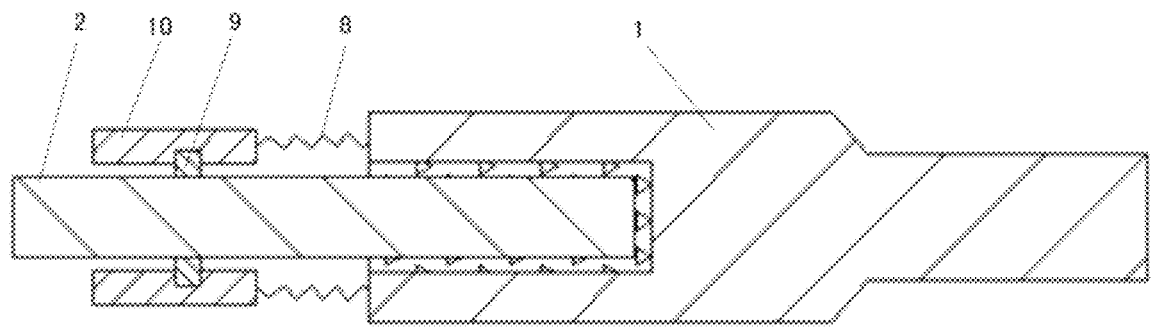
FIG. 6 is a schematic structural diagram of installing a split-type elastomer seal.
Figure 11:
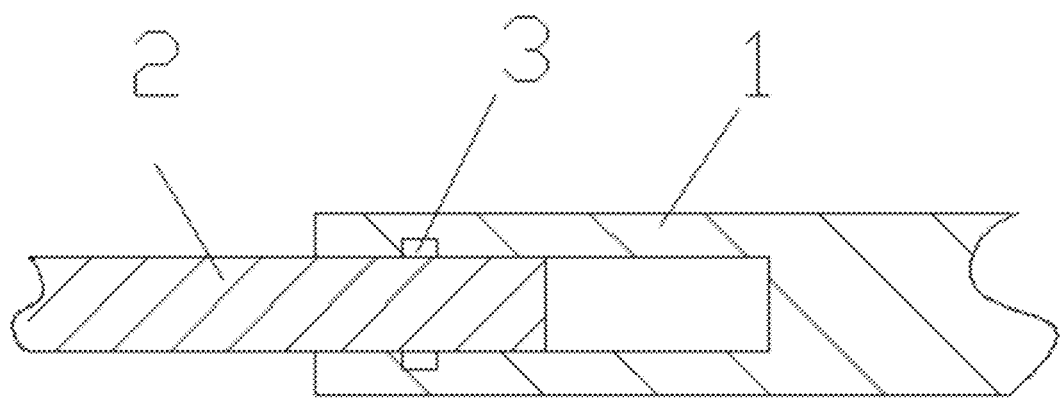
FIG. 11 is a sealing structure of an existing implant.
Figure 12:
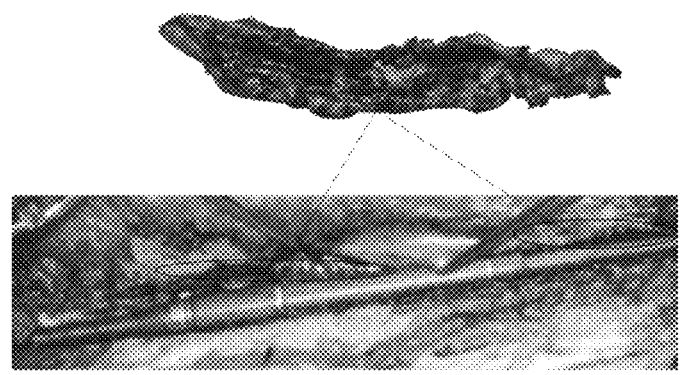
FIG. 12 is a schematic diagram of wear after a sealing form shown in FIG. 6 is used.

The elastomer seal can be further designed to be a split-type structure. As shown in FIG. 6, the elastomer seal mainly includes three parts: the flexible buffer part, a sealing ring, and a ferrule, an inner ring of the sealing ring is tightly sleeved on the inner component, an outer ring of the sealing ring is tightly fixed by the ferrule and the outer ring of the sealing ring and the ferrule both cannot move relatively, one end of the flexible buffer part is fixed and connected to the ferrule, and the other end is fixed and connected to an end head of the outer component. In this case, a micro-motion between the inner component and the outer component can be absorbed by the buffer part segment. Only when a relative motion between the implant components is relatively large, the sealing ring can move relative to the inner component. The structure is a direct improvement of the existing sealing structure (FIG. 11). The difference lies in an arrangement of the flexible buffer part, which minimizes a relative motion between the sealing ring and the inner component.

The in vivo implant of orthopedics of the present invention is an in vivo implant in which components move relatively, and the implant has a wide variety of structures. Specific examples are as follows:

Example 1

Figure 7:
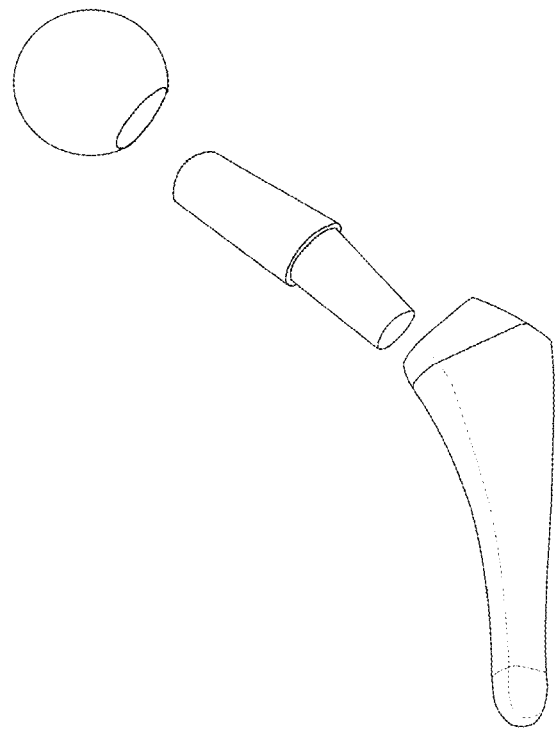
FIG. 7 is a schematic diagram of an implant (hip prosthesis assembled in an insertion manner)

Example 1 is a hip prosthesis assembled in an insertion manner as shown in FIG. 7. The insertion segment of the prosthesis implant is cone-shaped. Therefore, the outer component of the prosthesis has a special-shaped structure and an outer surface of the outer component is a non-smooth surface. An inner sleeve-type connection structure of the elastomer seal of FIG. 3, FIG. 4 or FIG. 5 can be adopted.

Example 2

Figure 8:
FIG. 8 is a schematic diagram of an implant (growth guide rod)

For the growth guide rod as shown in FIG. 8, the inner component and the outer component are connected through splines, and an outer sleeve-type elastic sealing manner as shown in FIG. 1 or 2 is adopted.

Example 3

Figure 9:
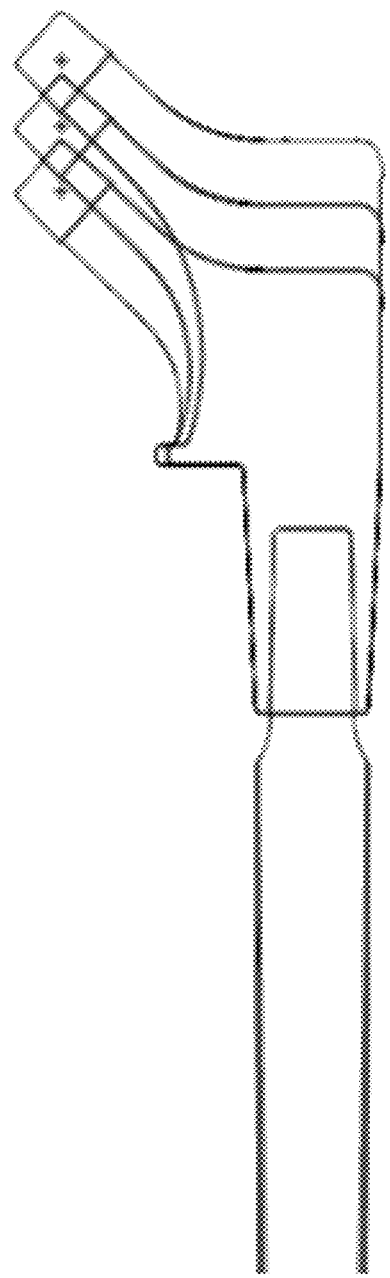
FIG. 9 is a schematic diagram of an implant (hip prosthesis assembled in an insertion manner)

For the hip prosthesis assembled in an insertion manner as shown in FIG. 9, the insertion segments of the inner component and the outer component of the prosthesis is also cone-shaped, which is similar to Example 1. A connection structure of the elastomer seal of FIG. 3, FIG. 4 or FIG. 5 can be adopted for the similar cone-shaped insertion segment or the cylindrical insertion segment.

Example 4

Figure 10:
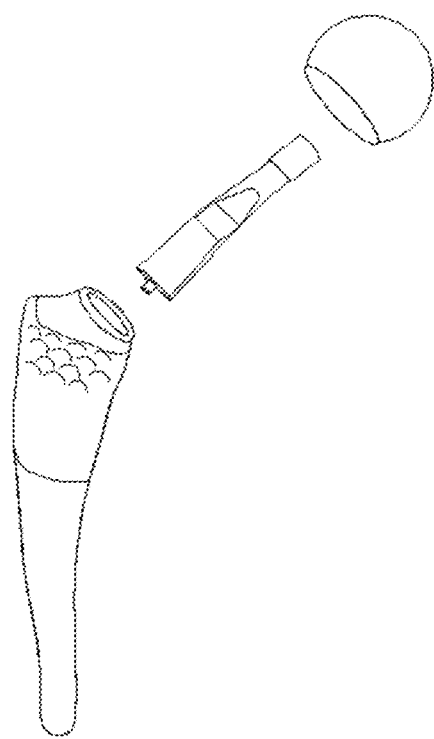
FIG. 10 is a schematic diagram of an implant (hip prosthesis with a replaceable femoral neck)

For the hip prosthesis with a replaceable femoral neck as shown in FIG. 10, the insertion segment of the prosthesis in vivo implant has an elliptical flat special-shaped structure, and because the outer component of the in vivo implant also has a special-shaped non-smooth surface structure, a connection structure of the elastomer seal of FIG. 3, FIG. 4 or FIG. 5 can be adopted.

Therefore, the in vivo implant of the present invention is various in structures and can be based on ORTHOPAEDIC ROD IN AUTOMATIC-EXTENDING AND ANTI-REVOLVING SCOLIOSIS CORRECTING SYSTEM disclosed in Chinese patent CN101785695B, where the orthopedic rod includes a sleeve and an insertion rod insertable into the sleeve; As shown in Spine Volume 43, Number 1, pp E16-E22, the magnetic growth rod; and an extending femoral nail. The orthopedic rod may also be a special-shaped piece with a fitting structure, such as a growth guide rod, for example an adjustable femoral nail. For example, in The Journal of Bone and Joint Surgery 2014; 96:488-93 dhttp://dx.doi.org/10.2106/JBJS.L.01625, at the joint between the femoral stem and the femoral neck of the hip prosthesis with a replaceable femoral neck. Any hip prosthesis assembled in an insertion manner and the like can be sealed by using the method of the present invention. Because the seal is of an elastic structure, whatever shape structure the in vivo implant has, self-adaptive tight connection between the seal and the in vivo implant component can be effectively ensured.

Contrast Example

Figure 13:
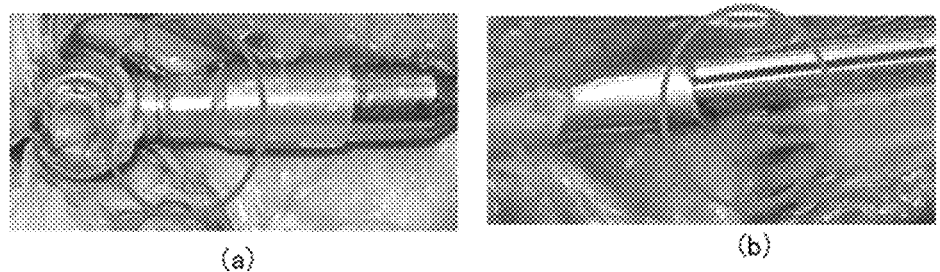
FIG. 13 is a comparison diagram before and after a sealing method of the present invention is adopted.

FIG. 13a is an in vivo implant of orthopedics that uses a wear debris limiting structure according to the present invention. After implanted into a 3-month-old sheep, as the sheep grows up, the growth rod lengthens, although there is sliding between the seal and the in vivo implant, the wear debris in the in vivo implant is still limited within the seal, and almost no wear debris escapes. FIG. 13b shows a situation in sheep of the same size correspondingly using a common in vivo implant (that is, without sealing treatment). Even after black-and-white treatment of the picture, four obvious black marks is still visible on the lower right part of a round frame, and a trace of debris escaping is very obvious.

To sum up, by using the method according to the present invention, contact between wear debris and patient bodies is reduced effectively, an opportunity of producing adverse effects is decreased, and the elastomer seal described in the present invention makes full use of a flexible annular part of the elastomer seal. Wear of the seal due to relative motion between the implant components can be effectively offset or reduced through the flexible buffer part.

Meanwhile, several micropores are distributed on the elastomer seal for balancing an internal pressure and an external pressure of the elastomer seal. The elastomer seal has an integrated structure. Micropores may be directly arranged on the elastomer seal. When the elastomer seal has a split-type structure, the micropores may be arranged on the buffer part, the ferrule or the seal body.

Figure 14:
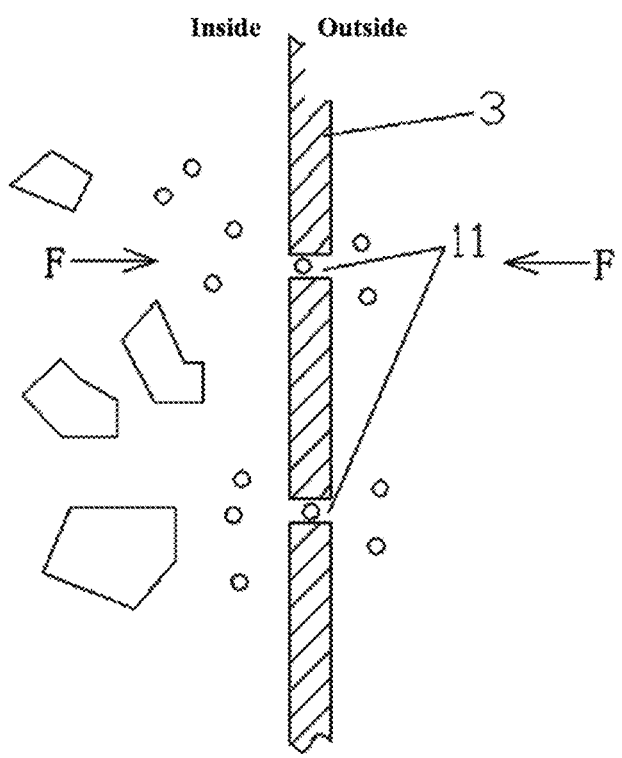
FIG. 14 is a schematic structural diagram 1 of micropores.

As shown in FIG. 14, the elastomer seal is a microporous structure that is in a normal open state in a natural state. Diameters of the micropores are smaller than those of the wear debris, allowing substances with small diameters such as water molecules to pass through, while large particles such as the wear debris cannot pass through, thus ensuring that the wear debris is not discharged.

Figure 15:
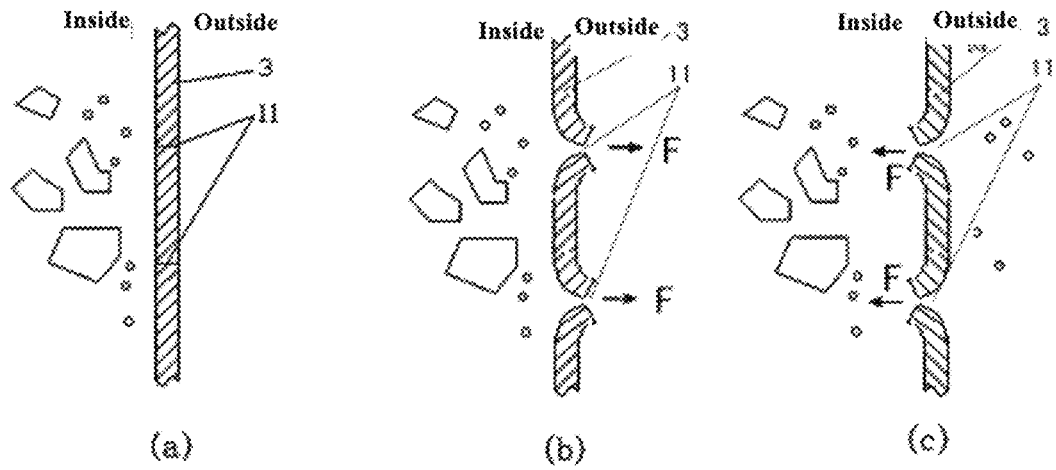
FIG. 15 is a schematic structural diagram 2 of micropores and a schematic dynamic diagram of the micropores.

As shown in FIG. 15a, the elastomer seal is a microporous structure that is in a closed state in a natural state. When pressures on both sides of the seal are not equalized, the seal can be automatically open to allow small-diameter substances such as water molecules to pass through, thereby balancing the pressure. Diameters of micropores in an open state (FIGS. 15b and 15c) are smaller than those of the wear debris, allowing substances with small diameters such as water molecules to pass through, while particles such as the wear debris cannot pass through.

Figure 16:
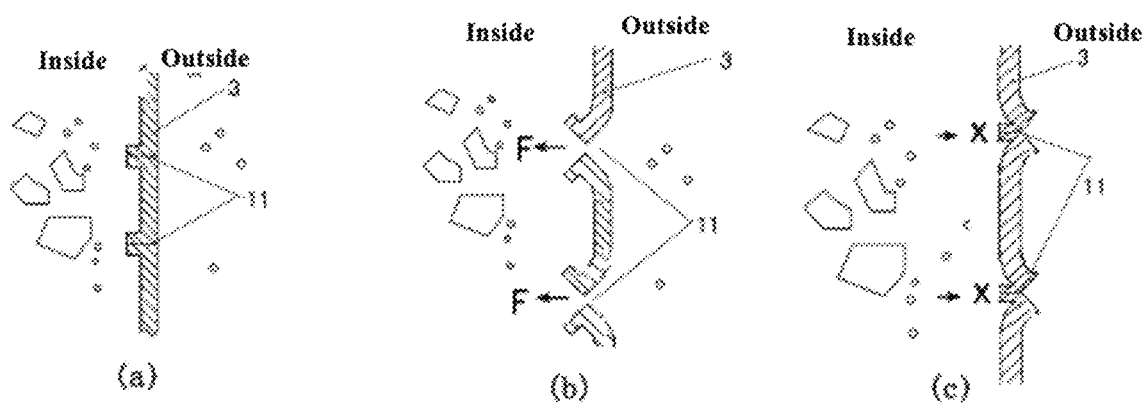
FIG. 16 is a schematic structural diagram 3 of micropores and a schematic dynamic diagram of the micropores.

As shown in FIG. 16a, the elastomer seal is a microporous structure having a function of realizing unidirectional flow. Diameters of the micropores when opened may be smaller or larger than those of the wear debris. Only when an internal pressure of the sealing space is small can the micropores be opened, that is, a pressurized state shown in FIG. 16b. When the micropores are opened, only external liquid and substances can enter due to the pressure, while neither wear debris particles nor water molecules inside can flow outwards, as shown in FIG. 16c.

Diameters of the water molecules and the wear debris particles are significantly different. Generally, particles of wear debris are more than 5 nanometers, most of them more than 1 micrometer and have relatively large diameters, while the water molecules and the like have diameters less than 1 nanometer and have relatively small diameters. By using an existing mature microporous semi-permeable membrane technology, passage of water molecules, ions and the like can be realized, while large molecules such as proteins and colloids cannot pass through. The semi-permeable membrane technology can be applied to meet the technical requirements of this patent. When processing materials such as PU, silica gel, and the like, even if micropores are large, a small amount of small-diameter wear debris may seep out, and most of the wear debris still cannot escape, thus greatly reducing harm of the wear debris.

The invention claimed is:

1. A method for limiting diffusion of wear debris of an in vivo implant, wherein an elastomer seal is arranged at a wearing part between implant components of the implant that can move relatively and generate wear, such that an outlet for wear debris of the implant is always sealed within a sealing area formed by the seal and the implant components, thereby preventing the wear debris from diffusing outwards;
wherein the implant components comprises an inner component and an outer component, wherein the inner component comprises an end slidably received within a complementary axial chamber formed within an end of the outer component, wherein the inner component and the outer component are capable of axially moving relative to each other and capable of generating wear debris from said axial movement, and wherein the outlet for wear debris of the implant is located at a port of the outer component that is cooperatively connected to the inner component;
wherein the elastomer seal comprises a sleeve including an end tightly attached to an outer wall of the inner component in proximity to said port, an opposite end tightly attached to an outer wall of the outer component in proximity to said port, and a flexible buffer part located between said ends of the elastomer seal and positioned at the outlet for wear debris of the implant; the flexible buffer part sized and configured for reducing or completely offsetting relative axial motion stroke between the implant components, thereby further reducing wear of a sealing part of the elastomer seal due to the relative motion between the implant components; the elastomer seal is adapted for sliding relative to the implant components when the flexible buffer part is insufficient to offset an axial motion stroke between the implant components;
wherein the flexible buffer part is an elastic deformation volume and/or an additional axial retractable structure of the elastomer seal; and
wherein the elastomer seal comprises medical silica gel or polyurethane (PU).

2. The method for limiting diffusion of wear debris of the in vivo implant according to claim 1, wherein several micropores are evenly distributed on the elastomer seal for balancing an inner side pressure and an outer side pressure of the seal.

* * * * *